(12) United States Patent
Yamashita (10) Patent No.: US 10,182,929 B2
(45) Date of Patent: Jan. 22, 2019

(54) STENT DELIVERY SYSTEM

(71) Applicant: Terumo Kabushiki Kaisha, Tokyo (JP)

(72) Inventor: Masao Yamashita, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 554 days.

(21) Appl. No.: 13/940,677

(22) Filed: Jul. 12, 2013

(65) Prior Publication Data

US 2013/0304187 A1  Nov. 14, 2013

Related U.S. Application Data

(63) Continuation of application No. PCT/JP2012/050046, filed on Jan. 5, 2012.

(30) Foreign Application Priority Data

Feb. 24, 2011 (JP) .................................. 2011-038856

(51) Int. Cl.
*A61F 2/962* (2013.01)
*A61F 2/966* (2013.01)
(Continued)

(52) U.S. Cl.
CPC .............. *A61F 2/962* (2013.01); *A61F 2/966* (2013.01); *A61F 2002/9517* (2013.01);
(Continued)

(58) Field of Classification Search
CPC .... A61F 2/95; A61F 2002/9665; A61F 2/966; A61F 2/2436
See application file for complete search history.

(56) References Cited

U.S. PATENT DOCUMENTS

2001/0049547 A1* 12/2001 Moore ...................... A61F 2/95
623/1.11
2002/0045929 A1  4/2002 Diaz
(Continued)

FOREIGN PATENT DOCUMENTS

CN  2857888 Y  1/2007
CN  101151003 A  3/2008
(Continued)

OTHER PUBLICATIONS

International Search Report (PCT/ISA/210) dated Apr. 17, 2012, by the Japanese Patent Office as the International Searching Authority for International Application No. PCT/JP2012/050046.
(Continued)

*Primary Examiner* — Katrina Stransky
*Assistant Examiner* — Michael Mendoza
(74) *Attorney, Agent, or Firm* — Buchanan Ingersoll & Rooney PC (57) ABSTRACT

A stent delivery system is configured to include an outer tube and an inner tube, with a space between the inner and outer tubes. In the space between the outer tube and the inner tube, a cylindrical mesh reinforcing spacer is provided at a position that is on the base end side of a stent. The reinforcing spacer is provided to be freely movable in the axial direction and radial direction. Even when the outer tube and the inner tube, which have been advanced into the lumen of a living body, are bent, the reinforcing spacer moves in the axial and radial directions and elastically deforms, thereby maintaining a substantially uniform internal circumference for the outer tube along the axial direction.

10 Claims, 11 Drawing Sheets

(51) Int. Cl.
*A61F 2/95* (2013.01)
*A61F 2/958* (2013.01)

(52) U.S. Cl.
CPC .............. *A61F 2002/9522* (2013.01); *A61F 2002/9583* (2013.01); *A61F 2002/9665* (2013.01)

(56) References Cited

U.S. PATENT DOCUMENTS

| | | | |
|---|---|---|---|
| 2002/0161425 A1* | 10/2002 | Hemerick | A61F 2/95 623/1.11 |
| 2003/0114910 A1 | 6/2003 | Juhani Laakso et al. | |
| 2003/0144671 A1 | 7/2003 | Brooks et al. | |
| 2004/0176740 A1 | 9/2004 | Chouinard | |
| 2005/0061771 A1* | 3/2005 | Murphy | A61M 25/0012 216/17 |
| 2006/0074477 A1 | 4/2006 | Berthiaume et al. | |
| 2006/0259124 A1 | 11/2006 | Matsuoka et al. | |
| 2006/0265047 A1 | 11/2006 | Dorn | |
| 2007/0032860 A1* | 2/2007 | Brooks | A61F 2/95 623/1.23 |
| 2007/0060880 A1 | 3/2007 | Gregorich et al. | |
| 2007/0265637 A1* | 11/2007 | Andreas | A61F 2/962 606/108 |
| 2009/0143849 A1 | 6/2009 | Ozawa et al. | |
| 2009/0281610 A1 | 11/2009 | Parker | |
| 2010/0049297 A1 | 2/2010 | Dorn | |
| 2010/0137966 A1* | 6/2010 | Magnuson | 623/1.11 |

FOREIGN PATENT DOCUMENTS

| | | |
|---|---|---|
| CN | 101450019 A | 6/2009 |
| JP | 2002-525168 A | 8/2002 |
| JP | 2006-525834 A | 11/2006 |
| JP | 2008-110132 A | 5/2008 |
| JP | 2009-506839 A | 2/2009 |
| JP | 2010-279795 A | 12/2010 |
| WO | WO 00/18330 A1 | 4/2000 |
| WO | WO 2004/098692 A1 | 11/2004 |
| WO | 2008/066917 A1 | 6/2008 |

OTHER PUBLICATIONS

Office Action (Notification of First Office Action) dated Dec. 26, 2014, by the Chinese Patent Office in corresponding Chinese Patent Application No. 201280003899.1, and an English Translation of the Office Action. (13 pages).

Second Office Action dated Aug. 6, 2015, by the State Intellectual Property Office of the People's Republic of China in corresponding Chinese Patent Application No. 201280003899.1 and an English translation of the Office Action (13 pgs).

European Search Report dated May 11, 2016, by the European Patent Office in corresponding European Application No. 12748901.1 (9 pages).

* cited by examiner

STENT DELIVERY SYSTEM

This application is a continuation of International Application No. PCT/JP2012/050046 filed on Jan. 5, 2012, and claims priority to Japanese Patent Application No. 2011-038856 filed on Feb. 24, 2011, the entire content of each of which is incorporated herein by reference.

TECHNICAL FIELD

The present invention generally relates to a stent delivery system for delivering and indwelling a stent into a lumen of a living body.

BACKGROUND DISCUSSION

Conventionally, there have been cases where a stent formed from metallic wire or the like in the shape of a hollow cylinder having a multiplicity of openings in its side wall and which is expandable in a lumen of a living body, such as blood vessel, bile duct, trachea, esophagus, urethra, etc., is used for improvement of a lesion part (stenosed part or obliterated part) in the lumen of the living body.

For instance, a stent having a self-expanding function (self-expandable stent) is delivered into a lumen of a living body while in a compressed state and contained in a gap between an inner tube and an outer tube, in a distal portion of a delivery catheter having the outer tube disposed over the periphery of the inner tube. Then, the outer tube is retracted proximally to release and expand the stent, whereby the stent can be put indwelling in the lesion part. In the stent delivery system having the stent and the catheter of this kind, there are cases where, for example, the outer tube and the inner tube are inserted into a winding lumen of a living body and are advanced into a lesion part. In this case, the space provided between the outer tube and the inner tube may cause bending and buckling of the outer tube.

In view of this, there has been known, as for example disclosed in JP-T-2002-525168 and JP-T-2006-525834, a stent delivery system wherein a coiled spring is provided between an outer tube and an inner tube so that the outer tube can be supported when the outer tube and the inner tube are bent in a lumen of a living body.

In the stent delivery system disclosed in JP-T-2002-525168 and JP-T-2006-525834, however, both ends of the coiled spring are connected (fixed) to the proximal end (base end) of the stent and the inner tube. When the inner tube and the outer tube are bent, therefore, the spring provided inside cannot follow up to the bending, so that stress concentration occurs at the contact point where the spring makes contact with the inner circumferential surface of the outer tube. As a result, the bent outer tube cannot be evenly supported by the spring. In addition, kinking (sharp bending) may take place, with the contact point between the bent outer tube and the spring as a starting point. In such a situation, the distal ends of the outer tube and the inner tube of the stent delivery system cannot be delivered into a desired portion in a lumen of a living body.

SUMMARY

According to one aspect, a stent delivery system for indwelling a stent in a lumen of a living body comprises: an inner tube; an outer tube surrounding the inner tube so that a gap exist between an inner surface of the outer tube and an outer surface of the inner tube, with the outer tube being axially movable relative to the inner tube; a radially outwardly extending stent locking part fixed relative to the inner tube; and a radially inwardly compressed stent positioned in the gap between the inner surface of the outer tube and the outer surface of the inner tube so that the stent is covered by the outer tube. The stent is configured to expand outwardly upon the outer tube being moved proximally relative to the inner tube so that the stent is exposed, the stent possessing opposite distal and proximal ends both positioned distally of the stent locking part. A reinforcing member is positioned in the gap between the inner surface of the outer tube and the outer surface of the inner tube, and the reinforcing member possesses proximal-most and distal-most ends positioned proximally of the stent locking part. The reinforcing member possesses a plurality of through holes and is configured to bend when the inner and outer tubes are bent, and the entire reinforcing member is movable in axial and radial directions relative to the inner and outer tubes.

According to another aspect, a stent delivery system for indwelling a stent in a lumen of a living body comprises: an inner tube; a stent disposed on a distal-side outer surface of the inner tube and being compressed toward a center axis of the stent when inserted into a lumen of a living body, and restorable to a pre-compression expanded shape by being expanded outwardly when indwelled in the lumen of the living body; an outer tube containing the stent in an inner lumen of the outer tube and disposed outwardly of the inner tube so that an inner surface of the outer tube faces an outer surface of the inner tube, with the outer tube being movable relative to the inner tube to release the stent to outside the outer tube by moving in a proximal direction relative to the inner tube; and a reinforcing member movable in axial and radial directions, and positioned between the outer tube and the inner tube proximal to the stent.

The stent delivery system is configured so that the outer tube is inhibited or prevented from kinking, and the outer tube and an inner tube can be assuredly delivered into a desired portion in a lumen of a living body. Accordingly, even in the case where the outer tube and the inner tube are inserted into a lumen of a living body and where the outer tube and the inner tube are bent according to the path of the lumen, the reinforcing member moves in the axial and radial directions within the space between the outer tube and the inner tube according to the bent state of the tubes, and, simultaneously, deforms elastically so as to be bent. As a result, the inner circumferential surface of the outer tube thus bent is substantially evenly supported by the moved and deformed reinforcing member, so that kinking (sharp bending) of the outer tube inside the lumen can be prevented from occurring. Therefore, the distal ends of the outer tube and the inner tube can be assuredly advanced to a desired portion in the lumen of the living body, and the stent can be delivered into the desired portion.

DETAILED DESCRIPTION

Figure 1:
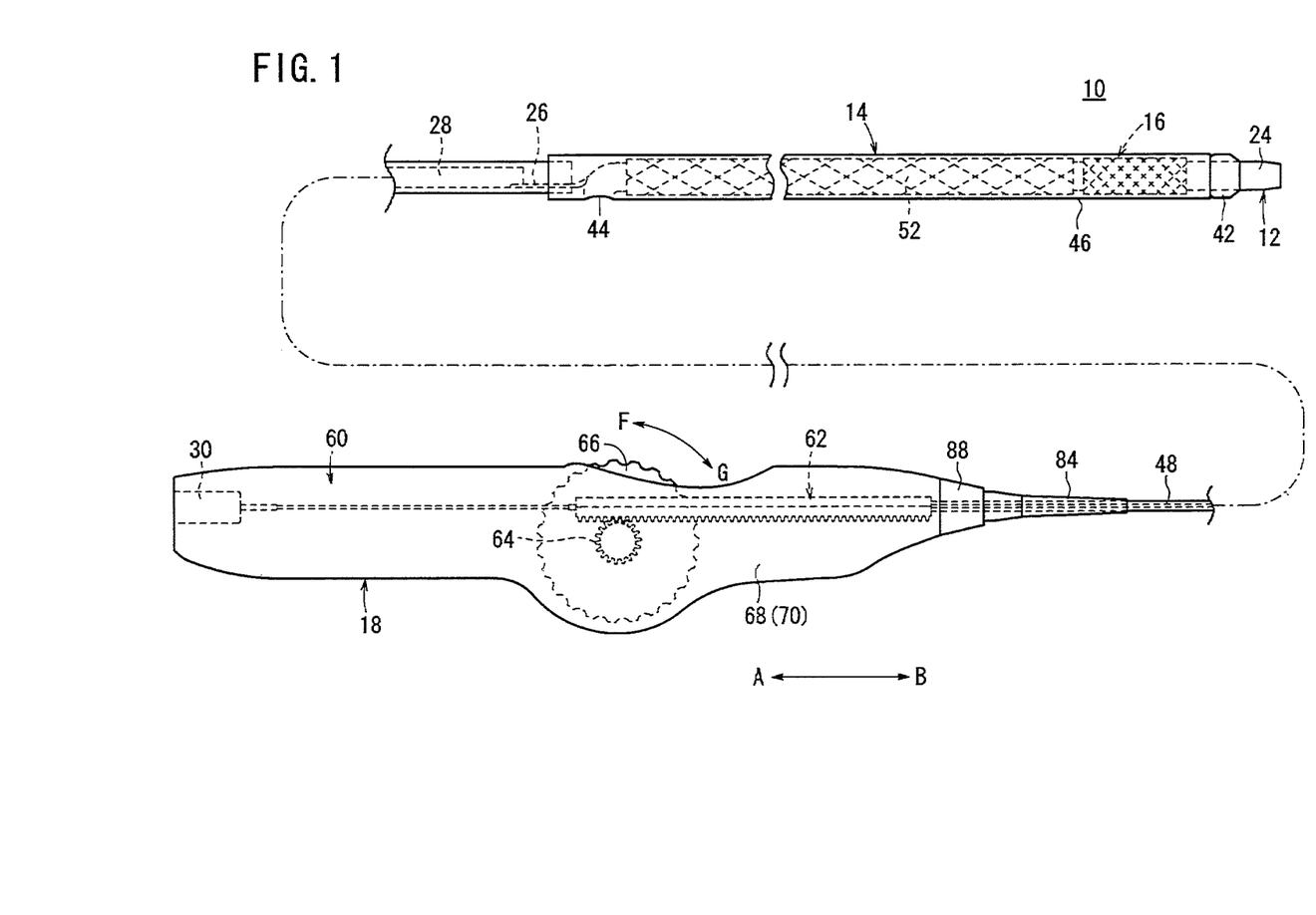
FIG. 1 is a side view of a stent delivery system according to an embodiment disclosed here.

FIG. 1 illustrates a stent delivery system 10 according to an embodiment disclosed here. The stent delivery system 10 includes an inner tube 12 formed in a tubular shape, an outer tube 14 provided on the outer circumference side of the inner tube 12, an expandable stent 16 positioned between the inner tube 12 and the outer tube 14, and an operating unit 18 for moving the outer tube 14 relative to the inner tube 12.

In FIG. 1, the left side of the inner tube 12 and the outer tube 14 is referred to as the "proximal end" or "rear end" side (the direction of arrow A), and the right side of the inner tube 12 and the outer tube 14 is referred to as the "distal end" or "front end" side (the direction of arrow B). This same nomenclature applies also to the other drawing figures.

Figure 2:
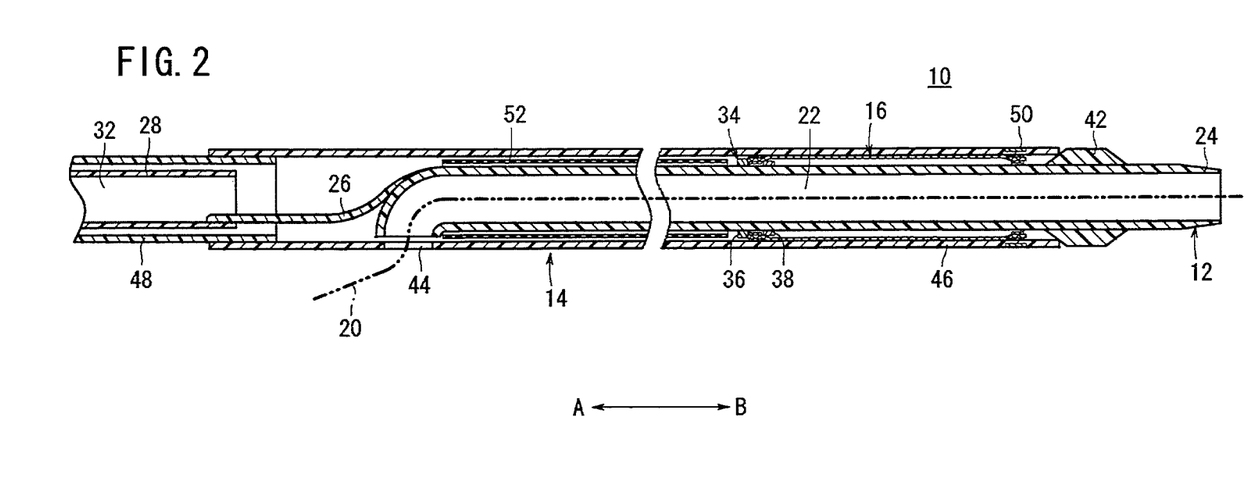
FIG. 2 is a partially omitted longitudinal cross-sectional view of an inner tube and an outer tube of the stent delivery system shown in FIG. 1.
Figure 3:
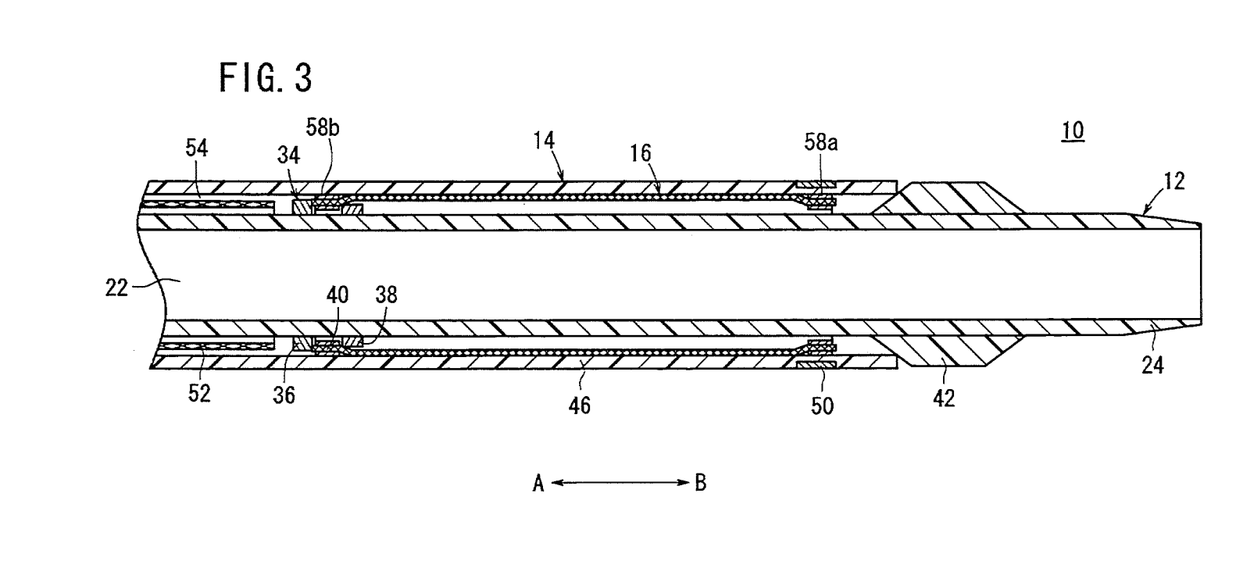
FIG. 3 is an enlarged longitudinal cross-sectional view of a distal end of the inner tube and the outer tube shown in FIG. 2.

As shown in FIGS. 1 to 4, the inner tube 12 includes a first distal tube 24 formed with a guide wire lumen 22 in which a guide wire 20 is to be inserted and passed (see FIG. 2), a first proximal tube 28 connected to the proximal end side (the direction of arrow A) of the first distal tube 24 through a connecting member 26, and a connector 30 connected to the proximal end of the first proximal tube 28. The inner tube 12 is composed of a tubular body. The distal end and the proximal end of the first distal tube 24 are each open, the distal end and the proximal end of the first proximal tube 28 are each open, and the distal end of the first distal tube 24 extends or protrudes distally beyond the distal end of the outer tube 14 as shown in FIGS. 1-3. The above-mentioned guide wire 20 is used, for example, for guiding the stent delivery system 10 to a lesion part in a lumen of a living body.

The inner tube 12 is so set that the proximal end of the first distal tube 24 and the distal end of the first proximal tube 28 are connected to each other through the connecting member 26 which is located in the inside of the outer tube 14. In addition, the first proximal tube 28 has a lumen 32 penetrating from the distal end of the first proximal tube 28 to the proximal end of the first proximal tube 28, and a liquid such as physiological saline is injected into the lumen 32 through the connector 30. It is preferable that the first distal tube 24 is formed from a highly flexible resin material, whereas the first proximal tube 28 is formed from a high-strength metallic material.

The first distal tube 24 is provided with a stent holding mechanism (holding mechanism) 34 by which movement of the stent 16 in the axial direction is restricted. As shown in FIG. 3, the stent holding mechanism 34 includes: a stent locking part 36 which is provided on an outer circumferential surface of the inner tube 12 and which is so provided as to be located on the proximal side (the direction of arrow A) of the stent 16 when the stent 16 is contained inside the outer tube 14; and a stent engaging part 38 which is provided on the distal side (the direction of arrow B) of the first distal tube 24 relative to the stent locking part 36 and with which a reduced diameter section 40 (described later) of the stent 16 is engaged.

The stent locking part 36 and the stent engaging part 38 are each formed in an annular shape, each project toward the radially outer side (radially outwardly) which is the outer tube 14 side, and are disposed with a predetermined spacing therebetween along the axial direction (the directions of arrows A and B) of the first distal tube 24. The height of the stent engaging part 38 is smaller than the height of the stent locking part 36.

This described configuration of the stent locking part 36 and the stent engaging part 38 helps ensure that in the condition wherein the stent 16 is contained in the inside of the outer tube 14, the proximal end of the stent 16 makes contact with the stent locking part 36, and the reduced diameter section 40 of the stent 16 is retained between the stent locking part 36 and the stent engaging part 38, whereby the stent 16 is retained in such a position that its distal end will not be exposed to the exterior via the distal end of a second distal tube 46. When the stent 16 is released via the distal end of the second distal tube 46, the proximal end of the stent makes contact with the stent locking part 36, whereby the stent 16 is expanded in the state of being positioned in a predetermined position.

When the stent 16 having been released to an intermediate extent is re-contained into the inside of the outer tube 14, its reduced diameter section 40 makes contact with the stent engaging part 38, whereby the stent 16 is retained in the state of being positioned in a predetermined position.

The first distal tube 24 is formed at its distal end with a stopper section 42 which bulges radially outward and by which movement of the outer tube 14 in the distal direction is restricted. This helps ensure that the outer tube 14 is inhibited from protruding in the axial direction (in the direction of arrow B) relative to the distal end of the inner tube 12. That is, the outer tube 14 is inhibited from protruding distally beyond the distal-most end of the inner tube 12.

On the other hand, the proximal end of the first distal tube 24 is gently curved toward a radially outer side (radially outwardly) of the first distal tube 24, to communicate with a guide wire leading-out hole 44 of the outer tube 14.

As shown in FIGS. 1 and 6-8, the connector 30 is formed in a hollow cylindrical shape, is connected to and communicates with the first proximal tube 28 of the inner tube 12, and is so formed that a liquid injector (for example, syringe) can be connected to the connector 30. Because the interior of the connector 30 is in communication with the interior of the first proximal tube 28, liquid injected into the connector 30 flows into the first proximal tube 28.

In the condition wherein the liquid injector is connected to the connector 30, a liquid is injected through the lumen 32 of the first proximal tube 28, and the liquid flows to the distal ends of the inner tube 12 and the outer tube 14, whereby the inside of each of these tubes can be flushed.

As shown in FIGS. 1-4, the outer tube 14 is composed of tubular bodies; specifically, the outer tube 14 includes the second distal tube 46 in which the first distal tube 24 of the inner tube 12 is disposed, and a second proximal tube 48 which is connected to the proximal side (the direction of arrow A) of the second distal tube 46 and in which the first proximal tube 28 is disposed. The distal end of the second distal tube 46 functions as a release port at the time of indwelling of the stent 16 in a lesion part in a lumen of a living body, and functions also as a containing port at the time of recovering the stent 16 having been released to an intermediate extent.

In addition, the second distal tube 46 is provided on its proximal side with the guide wire leading-out hole 44, as an opening through which the lumen of the second distal tube 46 and the exterior communicate with each other. The guide wire leading-out hole 44 is so provided that it can communicate with the opening of the guide wire lumen 22 of the first distal tube 24 provided inside the second distal tube 46. The guide wire 20 inserted and passed in the guide wire lumen 22 of the inner tube 12 can be lead out to the exterior through the guide wire leading-out hole 44.

Furthermore, a distal portion of the second distal tube 46 is provided with a contrast marker 50. The contrast marker 50 is on the outer circumferential surface of the distal portion of the second distal tube 46. The contrast marker 50 is annular in shape and formed from a radiopaque material, for example.

In the inside of the second distal tube 46, a cylindrical reinforcing spacer (reinforcing member) 52 is provided between the stent holding mechanism 34 provided on the inner tube 12 and the connecting member 26. The reinforcing spacer 52 is thus positioned on the proximal end side of the stent holding mechanism 34 and on the distal end side of the connecting member 26. The reinforcing spacer 52 is also positioned distally of the guide wire leading-out hole 44 in the outer tube. As shown in FIGS. 1 to 5, this reinforcing spacer 52 is formed in the shape of a mesh having a plurality of through openings. The reinforcing spacer 52 is formed from an elastic resin material, a metallic material, or a mixed material comprised of both resin material and metallic material.

Figure 4:
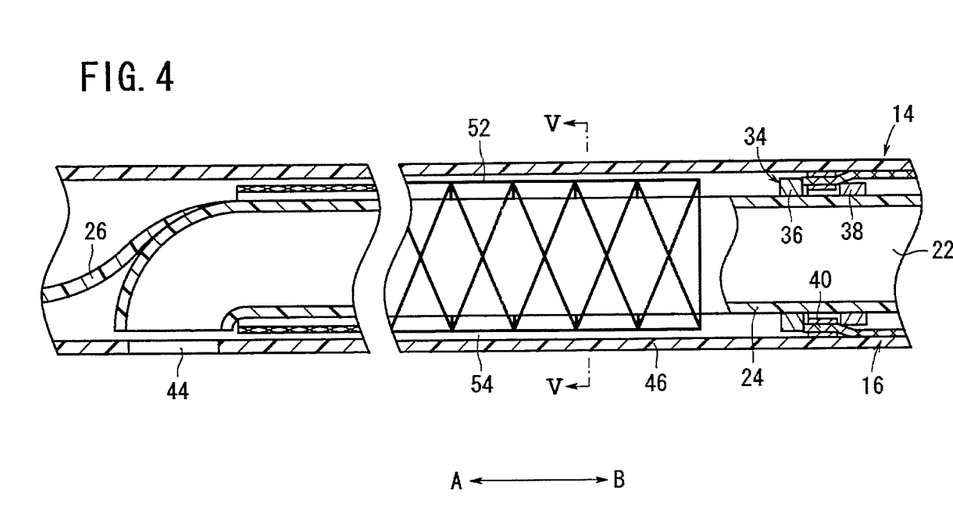
FIG. 4 is an enlarged longitudinal cross-sectional view of a portion of the stent delivery system in the vicinity of a reinforcing spacer shown in FIG. 2.

The reinforcing spacer 52 possesses a predetermined length in the axial direction (the direction of arrows A and B) and possesses a substantially constant diameter along the axial direction. More in detail, the reinforcing spacer 52 is formed in the shape of a mesh (network) having linear elements intersecting in directions substantially orthogonal to the axial direction as shown in FIG. 4.

Figure 5:
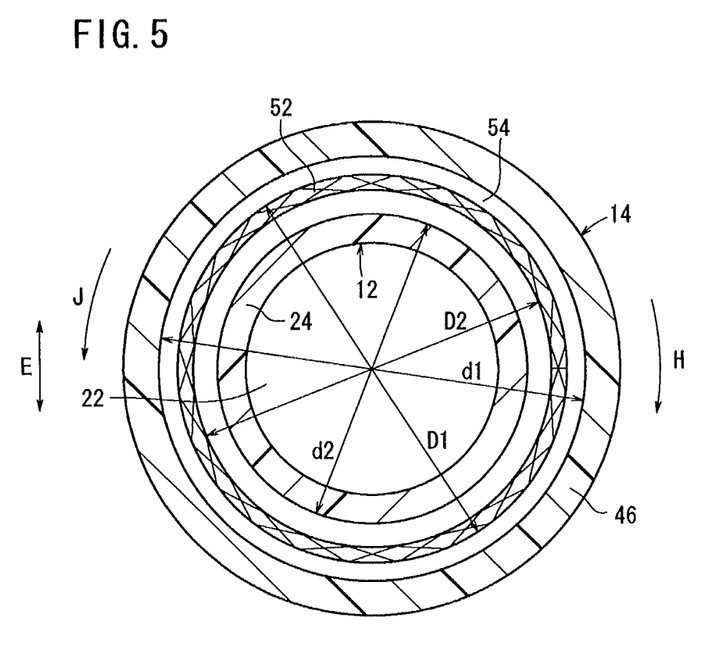
FIG. 5 is a transverse cross-sectional view taken along the section line V-V in FIG. 4.
Figure 6:
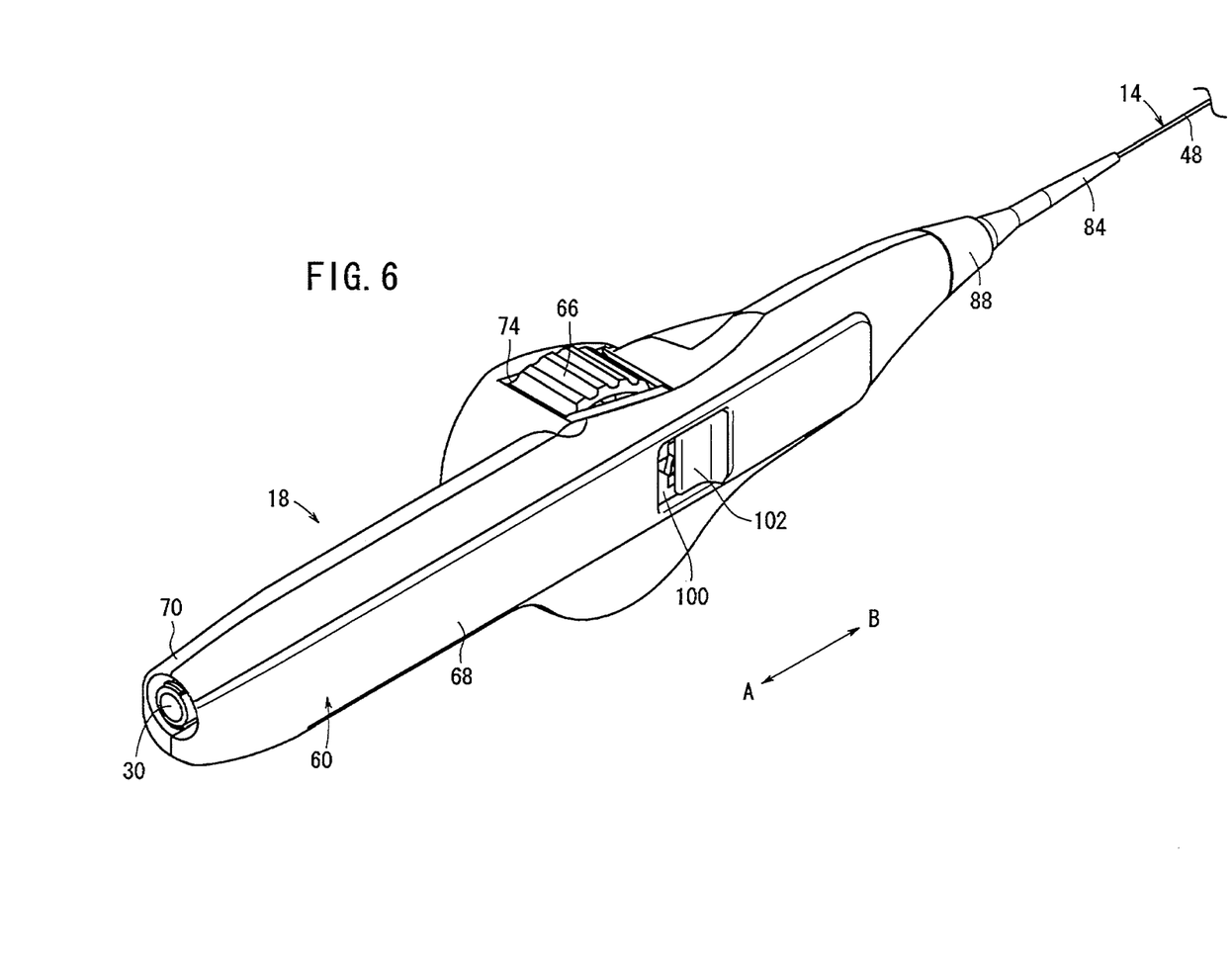
FIG. 6 is a perspective view of an operating unit of the stent delivery system shown in FIG. 1.

As shown in FIG. 5, the outside diameter D1 of the reinforcing spacer 52 is smaller than the inside diameter d1 of the second distal tube 46 of the outer tube 14, and the inside diameter D2 of the reinforcing spacer 52 is greater than the outside diameter d2 of the first distal tube 24 of the inner tube 12. Therefore, the reinforcing spacer 52 is movable in the radial direction (in the directions of arrows E) in a gap (space) 54 formed between the outer tube 14 and the inner tube 12.

In addition, the entire reinforcing spacer 52 is movable in the axial direction (in the directions of arrows A and B) between the stent locking part 36 of the stent holding mechanism 34 and the connecting member 26. Specifically, the reinforcing spacer 52 is not fixed relative to the outer tube 14 or the inner tube 12, but is movable in the axial direction (in the directions of arrows A and B) and in the radial direction (in the directions of arrows E) within the inside of the outer tube 14.

In other words, the reinforcing spacer 52 functions as a spacer for filling the gap 54 between the outer tube 14 and the inner tube 12.

As shown in FIG. 3, the stent 16 is formed in the shape of a mesh having a multiplicity of through openings, and in a substantially cylindrical shape. This stent 16 is a self-expandable stent which is disposed in the state of being compressed radially inward (in the direction toward the center axis) in the inside of the second distal tube 46 of the outer tube 14 at the time of insertion into a lumen of a living body, and which can be restored into its pre-compression shape through outward radial expansion upon being released via the distal end of the outer tube 14 to a lesion part in the lumen of the living body. The material constituting the stent 16 is preferably a superelastic metal such as Ni—Ti alloy, for example.

The stent 16 is provided at its distal end and proximal end with annularly shaped contrast markers 58a, 58b formed from a radiopaque material, for example. In addition, the stent 16 is provided at its proximal end with the reduced diameter section 40 where its diameter is reduced radially inward. The reduced diameter section 40 is so formed as not to make contact with the outer circumferential surface of the inner tube 12.

As shown in FIGS. 1 and 6-8, the operating unit 18 includes: a housing 60; a rack member 62 which is contained in the inside of the housing 60 and is connected to the outer tube 14; and a rotating roller 66 which has a first gear 64 meshed with the rack member 62 and by which the rack member 62 is displaced rectilinearly.

Figure 7:
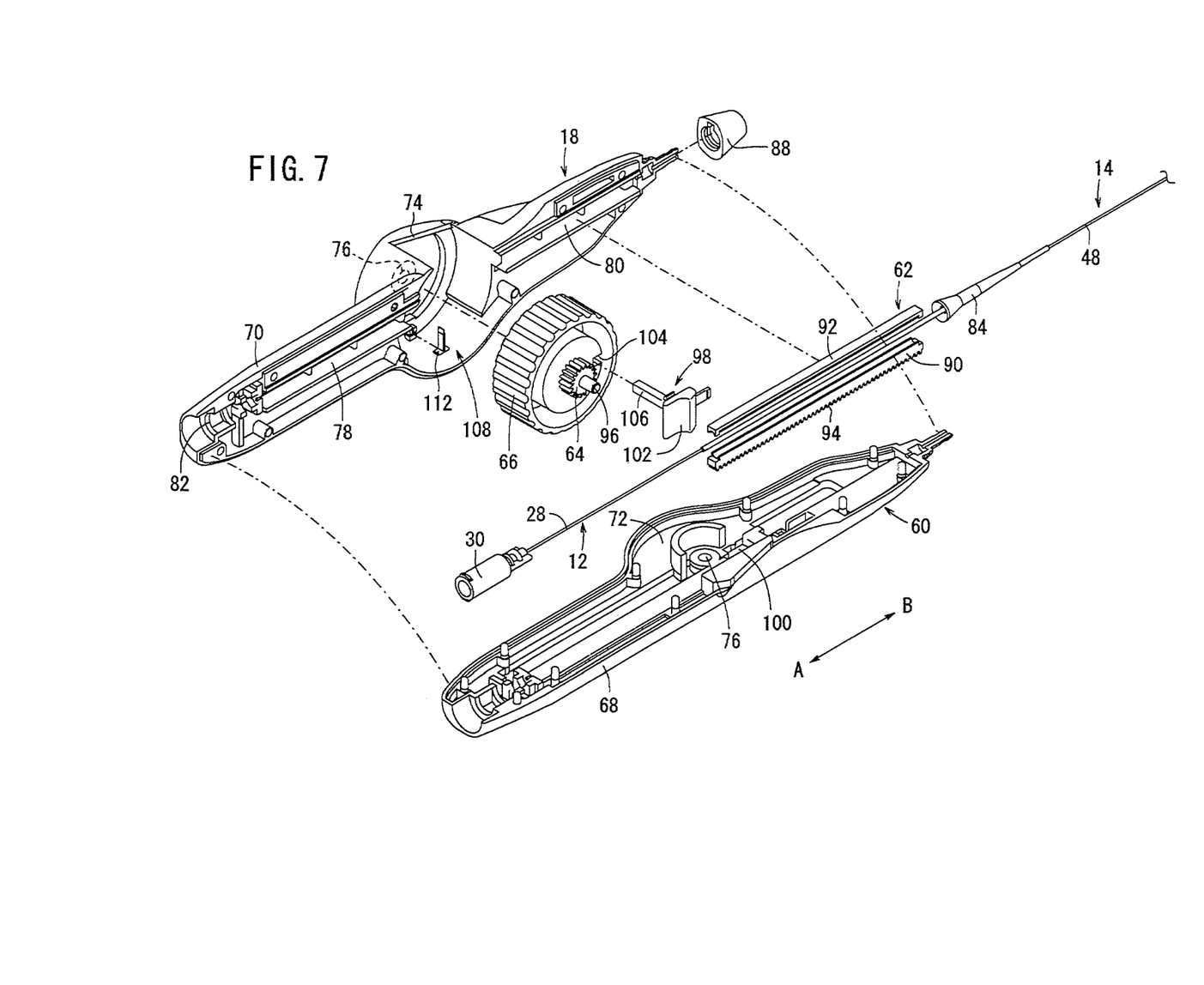
FIG. 7 is an exploded perspective view of the operating unit shown in FIG. 6.

The housing 60 is round-shaped at its central portion, and is composed of a first housing part 68 and a second housing part 70 into which the housing 60 is bisected at the center in the thickness direction of the housing. The housing 60 is provided, inside the first and second housings 68 and 70, with a roller containing section 72 configured to contain the rotating roller 66 in a central portion of the roller containing section 72. A part of the rotating roller 66 is exposed to the exterior through a roller hole 74 formed in the roller containing section 72. The rotating roller 66 is rotatably supported by a pair of bearings 76 formed at inner wall surfaces of the first and second housings 68 and 70.

In addition, the second housing 70 is formed with first and second containing grooves 78 and 80 in which the rack member 62 is contained and retained so as to be movable in the axial direction (in the directions of arrows A and B). The first containing groove 78 is provided on the proximal side (the direction of arrow A) in the second housing 70, while the second containing groove 80 is provided on the distal side (the direction of arrow B) in the second housing 70. The roller containing section 72 is disposed between the first containing groove 78 and the second containing groove 80.

With the first housing 68 and the second housing 70 combined with each other (engaged with or connected to each other), the rack member 62 is retained by the first and second containing grooves 78 and 80 in the state of being movable rectilinearly toward the distal end side and the proximal end side.

A connector containing section 82 which contains the connector 30 is formed on the proximal side (the direction of arrow A) of the first containing groove 78. The connector 30 is fixed to the housing 60 by being contained in the connector storing section 82. This results in the proximal end of the first proximal tube 28 constituting the inner tube 12 being fixed to the operating unit 18 through the connector 30.

The connector containing section 82 is open toward the proximal side (the direction of arrow A) of the housing 60, and is so formed that the liquid injector can be connected to the connector 30 from the exterior of the housing 60.

A distal nozzle 84 by which the second proximal tube 48 of the outer tube 14 is slidably retained is mounted to the distal end of the housing 60. The distal nozzle 84 is formed therein with a through-hole in which the second proximal tube 48 is positioned and through which the second proximal tube 48 is passed.

In the condition wherein the distal nozzle 84 is mounted to the distal end of the housing 60, a cap 88 is screw engaged onto the distal end of the housing 60, whereby the distal nozzle 84 is fixed. In other words, the outer tube 14, with the inner tube 12 inserted and passed therein, is inserted into the housing 60 through the distal nozzle 84, and is connected to the rack member 62.

The rack member 62 is composed of a pair of first and second blocks 90 and 92 which are formed in straight and substantially symmetric shapes. The proximal end of the second proximal tube 48 of the outer tube 14 is fixed by being clamped between the first block 90 and the second block 92. In this case, the inner tube 12 can be freely moved within the inside of the outer tube 14.

The rack member 62 composed of the first and second blocks 90 and 92 is positioned in the first and second containing grooves 78 and 80 inside the housing 60, whereby the rack member 62 is retained in the state of being rectilinearly movable toward the distal side and the proximal side of the housing 60.

In addition, the first block 90 is provided inside the housing 60 so as to front on the rotating roller 66, and its side surface fronting on the rotating roller 66 is provided with a plurality of tooth portions 94 defined by projections and recesses arranged along the axial direction (the direction of arrows A and B).

The rotating roller 66 is in the shape of a wheel having a predetermined width. A pair of rotating shafts 96 provided in a central portion of the rotating roller 66 are inserted respectively into the bearings 76 of the first and second housings 68 and 70. A first gear 64 with the rotating shafts 96 as a center is provided at a side surface of the rotating roller 66, and meshes with the tooth portion 94 of the rack member 62. When the rotating roller 66 is rotated, the rack member 62 is moved rectilinearly along the first and second containing grooves 78 and 80.

An outer circumferential portion of the rotating roller 66 is partly exposed to the exterior (outside the housing 60) through the roller hole 74 of the housing 60, and the operator rotates the rotating roller 66 by way of the exposed part.

Figure 8:
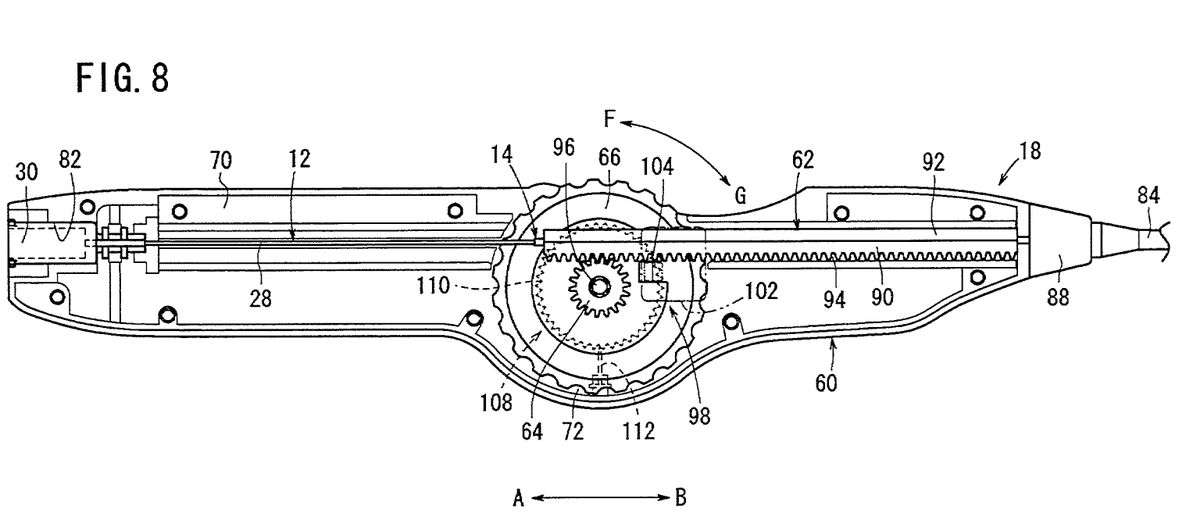
FIG. 8 is a side view of the inside of the operating unit shown in FIGS. 6 and 7.

In the operating unit 18 as above-described, for example, as shown in FIG. 8, the operator may rotate the rotating roller 66 in a predetermined direction relative to the housing 60 (in the direction of arrow F in FIG. 8). This results in the rack member 62 moving toward the connector 30 side (in the direction of arrow A) along the first and second containing grooves 78 and 80 in the inside of the housing 60. This results in the outer tube 14 moving (moving backward) toward the proximal side of the housing 60. Consequently, the stent 16 is released via the distal end of the outer tube 14.

On the other hand, when the rotating roller 66 is rotated in the direction opposite to the above-mentioned direction (in the direction of arrow G in FIG. 8) after the stent 16 is released to an intermediate extent, the rack member 62 is moved away from the connector 30 (in the direction of arrow B) along the first and second containing grooves 78 and 80. As a result of this, the outer tube 14 moves distally (moves forward) relative to the inner tube 12, whereby the stent 16 is re-contained into the inside of the outer tube 14.

In addition, as shown in FIGS. 7, 8, 10A and 10B, the operating unit 18 is provided with a locking mechanism 98 which can restrict a moving motion of the rack member 62 by restricting a rotating motion of the rotating roller 66. The locking mechanism 98 includes a slide member 102 provided in a hole 100 opening in a side surface of the first housing 68 so as to be displaceable by sliding, and a pin groove 104 formed in a side surface of the rotating roller 66 so as to front on the slide member 102.

Figure 10A:
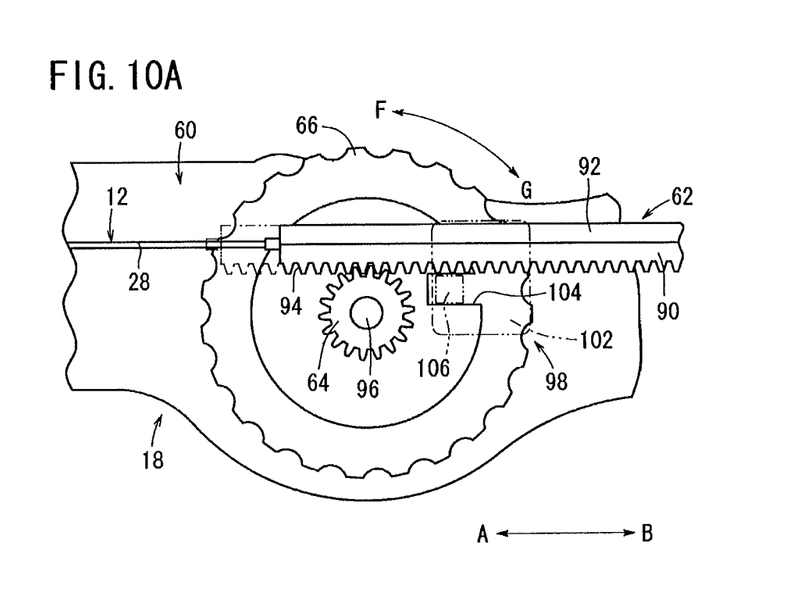
FIG. 10A is an operation illustration showing a locking mechanism provided in the operating unit in a state in which a pin is inserted in a pin groove.
Figure 10B:
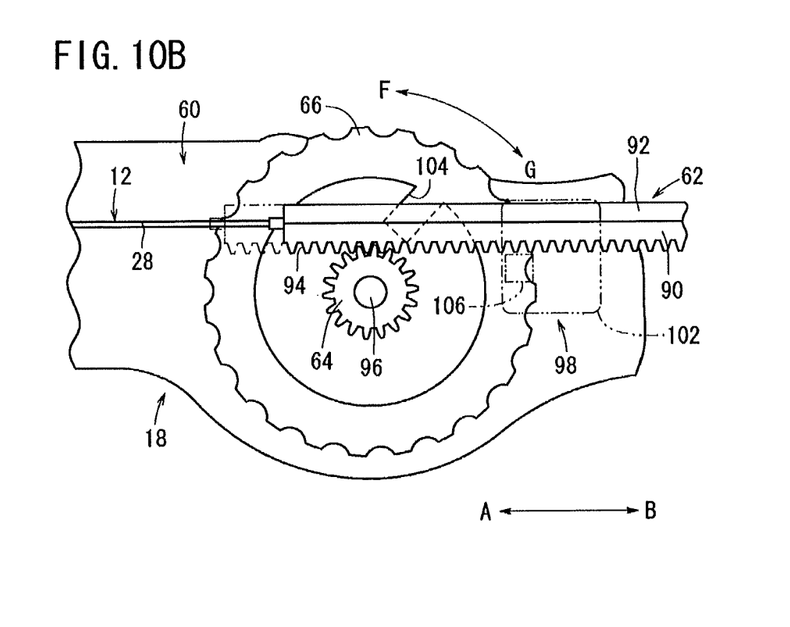
FIG. 10B is an operation illustration showing a state in which the pin is disengaged from the pin groove and the restriction imposed on rotation of a rotating roller is removed.

The slide member 102 is so retained as to be rectilinearly displaceable toward the distal side and the proximal side of the first housing 68 (in the directions of arrows A and B) through the hole 100. When a pin 106 that is rectangular in cross-sectional shape and projecting into the inside of the first housing 68 is positioned in the pin groove 104 of the rotating roller 66, in the condition wherein the slide member 102 is located on the proximal side in the housing 60, a rotating motion of the rotating roller 66 is restricted (prevented).

The pin groove 104 possesses a rectangular cross-sectional shape corresponding to the shape of the pin 106. Therefore, the rack member 62 would not be moved in the axial direction, and, accordingly, forward movement or backward movement of the outer tube 14 is restricted.

When the slide member 102 is moved toward the distal side of the housing 60 (in the direction of arrow B), the pin 106 is disengaged from the pin groove 104 in the radially outer direction of the rotating roller 66, whereby the restriction imposed on rotation of the rotating roller 66 by the pin 106 is removed. This results in a state wherein the rack member 62 can be moved in the axial direction (in the directions of arrows A and B) under a rotating action of the rotating roller 66.

Furthermore, the operating unit 18 is provided with an intermittent mechanism 108 for intermittently putting the rotating roller 66 into a rotating motion. The intermittent mechanism 108 includes: a second gear 110 provided at a side surface of the rotating roller 66 opposite to the first gear 64; and a notch member 112 which is retained by the second housing 70 and is engaged with the tooth portion of the second gear 110. The notch member 112 is formed, for example, in the shape of a thin sheet which is elastically deformable. The notch member 112 extends from a part retained by the second housing 70 toward the center of the second gear 110, and engages the tooth portion of the second gear 110.

When the rotating roller 66 is rotated, the notch member 112 engaged with the second gear 110 is elastically deformed, to be disengaged from a recess of the tooth portion and come over an adjacent projection to be again engaged with a recess, so that a rotating motion can be performed intermittently. Furthermore, from a sound generated upon engagement of the notch member 112 with the second gear 110, it is possible to confirm the rotating motion and a rotating angle of the rotating roller 66.

The operation and effect of the stent delivery system 10 will be described below. A state is assumed in which the guide wire 20 is inserted in a lumen of a living body (for example, a blood vessel), and its distal end has preliminarily been put indwelling in a lesion part in the lumen of the living body.

In such a preparatory state, flushing of the stent delivery system 10 shown in FIG. 1 is conducted.

First, the operator connects a liquid injector to the connector 30 provided at the proximal end of the operating unit 18, and injects a liquid from the liquid injector into the connector 30. As a result, the liquid flows through the lumen 32 of the first proximal tube 28 toward the distal side in the inner tube 12 (in the direction of arrow A), and flows into the outer tube 14 through the joint part between the first proximal tube 28 and the first distal tube 24. Then, the liquid having reached the distal end is ejected from the distal ends of the inner tube 12 and the outer tube 14, whereby flushing of the inside of the inner tube 12 and the outer tube 14 is completed in the exterior of a living body.

Next, as shown in FIG. 2, the proximal end of the guide wire 20 exposed to the exterior of the living body is inserted and passed via the distal end of the inner tube 12 into the guide wire lumen 22, and the inner tube 12 and the outer tube 14 are gradually advanced along the guide wire 20 into a lumen of a living body. The proximal end of the guide wire 20 is led out to the exterior of the outer tube 14 by way of the opening of the inner tube 12 and the guide wire leading-out hole 44 of the outer tube 14.

Figure 9:
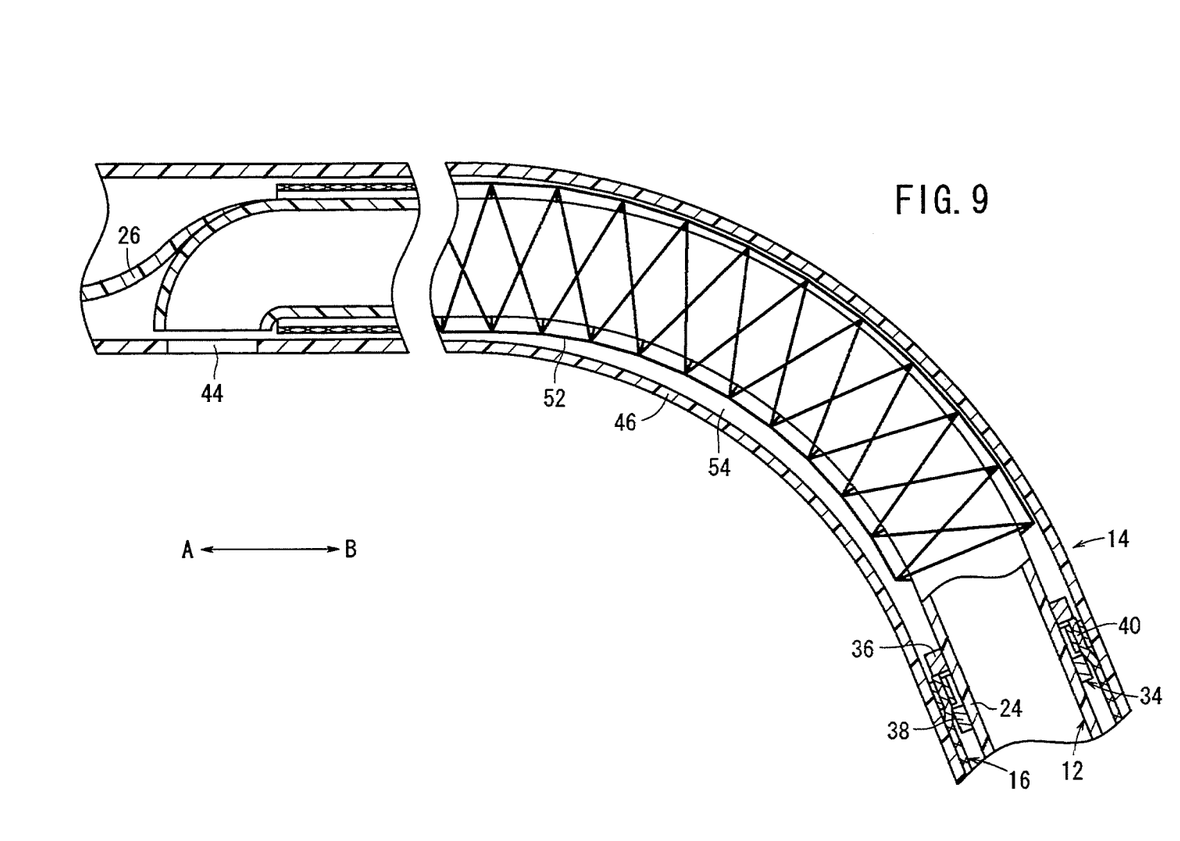
FIG. 9 is an enlarged longitudinal cross-sectional view showing a state in which the inner tube and the outer tube shown in FIG. 4 are bent.

In this case, when the inner tube 12 and the outer tube 14 are gradually advanced in the lumen of the living body, as shown in FIG. 9, the tubes may be bent when passing through a winding lumen. According to the bending shape of the outer tube 14, however, the reinforcing spacer 52 provided inside the outer tube 14 is moved in the axial direction (in the directions of arrows A and B) and the radial direction (in the directions of arrows E in FIG. 5) within the gap 54 between the outer tube 14 and the inner tube 12, and, simultaneously, the reinforcing spacer 52 is elastically deformed into an arcuate sectional shape so as to be bent.

More in detail, in a bent part of the lumen, the outer tube 14 and the inner tube 12 may be deformed in different manners. In such a case, the reinforcing spacer 52 is freely moved and elastically deformed within the gap 54 between the outer tube 14 and the inner tube 12, thereby retaining the inner circumferential surface of the outer tube 14 substantially evenly along the axial direction.

Furthermore, in a lumen, a stress in a moment direction (i.e., torque direction, in the direction of arrow H or J in FIG. 5) with the axis as a center may be applied to the inner tube 12 and the outer tube 14. In such a case, also, deformation of the outer tube 14 by the stress in the moment direction (in the direction of arrow H or J in FIG. 5) is restrained, since the reinforcing spacer 52 is formed in the shape of a mesh (network) with linear elements intersecting in directions substantially orthogonal to the axis.

In other words, the provision of the reinforcing spacer 52 makes it possible to enhance flexural rigidity and torsional rigidity of the outer tube 14.

After the arrival of the distal end of the outer tube 14 in a lesion part is confirmed by the contrast marker 50, the slide member 102 of the operating unit 18 is moved toward the distal end side (in the direction of arrow B), and the pin 106 is disengaged from the pin groove 104 of the rotating roller 66, whereby the restriction imposed on rotation of the rotating roller 66 is removed. Then, the rotating roller 66 is rotated in a predetermined direction (in the direction of arrow F in FIGS. 8, 10A and 10B).

As a result of the rotation of the first gear 64, the rack member 62 is moved proximally (in the direction of arrow A) within the housing 60. This is attended by gradual movement of the outer tube 14 toward the proximal side of the operating unit 18. In other words, the outer tube 14 is moved backward (retracted) relative to the inner tube 12.

Figure 11:
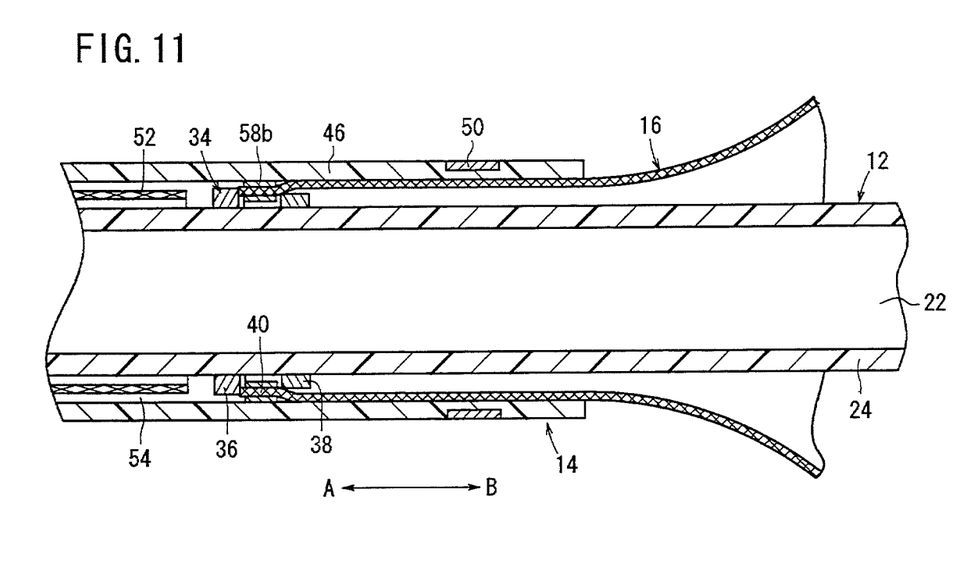
FIG. 11 is an enlarged longitudinal cross-sectional view showing a state in which the stent is released from the distal end of the outer tube to an intermediate extent, or a case wherein the stent released to an intermediate extent is contained in the inside of the outer tube.

As a result, as shown in FIG. 11, the stent 16 contained in the outer tube 14 starts being gradually exposed from its distal side; simultaneously, the stent 16 starts expanding radially outward. Then, the stent 16 comes into the state of being completely exposed from the outer tube 14, whereby the stent 16 is put indwelling (indwelled) in the lesion part in the state of being expanded in the cylindrical shape.

Finally, the inner tube 12 and the outer tube 14 constituting the stent delivery system 10 are withdrawn proximally (in the direction of arrow A), whereby they are removed to the exterior of the living body, with only the stent 16 left indwelling in the lesion part.

To readjust the indwelling position or the like of the stent 16 exposed (released) to an intermediate extent (partially exposed) in a lumen of a living body, the rotating roller 66 of the operating unit 18 is rotated in the direction opposite to the above-mentioned direction (i.e., the rotating roller 66 is rotated in the direction of arrow G in FIGS. 8, 10A and 10B). This results in the rack member 62 moving distally (in the direction of arrow A) within the housing 60, and, attendantly, the outer tube 14 is gradually moved toward the distal end of the inner tube 12. As a result, the outer circumferential surface of the stent 16 which was exposed is gradually covered by the outer tube 14 while being compressed radially inward by the distal end of the outer tube 14.

Then, the reduced diameter section 40 of the stent 16 comes into contact with the stent engaging part 38, whereby the stent 16 is contained in a predetermined position inside the outer tube 14 in the state of being again compressed radially inward, and is put into the state of being retained through the stent holding mechanism 34.

Thereafter, the inner tube 12 and the outer tube 14 are moved so that the stent 16 will be located in a desired position in the lesion part. Then, the rotating roller 66 is again rotated in the predetermined direction to move the outer tube 14 backward, whereby the stent 16 is again exposed, expanded, and put indwelling in the desired position. In this case, also, the inner circumferential surface of the outer tube 14 is retained substantially evenly along the axial direction, by movement and deformation of the reinforcing spacer 52.

As has been described above, the reinforcing spacer 52 formed, for example, from an elastic resin material or a metallic material and being in the shape of a mesh having a multiplicity of through openings is provided in the gap 54 between the second distal tube 46 (which constitutes the outer tube 14) and the first distal tube 24 (which constitutes the inner tube 12), in such a manner as to be freely movable in the axial direction (in the directions of arrows A and B) and in the radial direction (in the directions of arrows E).

This helps ensure that even in the case where the outer tube 14 and the inner tube 12 are advanced into a lumen of a living body and where the outer tube 14 and the inner tube 12 are bent in a winding lumen, the reinforcing spacer 52 is moved in the axial direction (in the directions of arrow A and B) and in the radial direction (in the directions of arrows E) within the gap 54 between the outer tube 14 and the inner tube 12 according to the bent state of the outer tube 14, and, simultaneously, the reinforcing spacer 52 is elastically deformed into an arcuate sectional shape so as to be bent.

As a result, the inner circumferential surface of the outer tube 14 is retained favorably and substantially evenly by the elastic reinforcing spacer 52. As a result of this, kinking of the outer tube 14 in the lumen is securely prevented, and the distal ends of the outer tube 14 and the inner tube 12 can be assuredly advanced into the lesion part in the lumen of the living body.

In other words, both ends of the reinforcing spacer 52 are not at all fixed to the stent holding mechanism 34 and the inner tube 12, and the reinforcing spacer 52 is disposed in a freely movable state for the purpose of filling the gap 54. Therefore, generation of kinking, which might occur in the related-art stent delivery system including a spring fixed at both ends to an inner tube or the like, can be avoided assuredly.

In the case where the reinforcing spacer 52 is formed in the shape of a mesh (network) having linear elements intersecting in directions substantially orthogonal to the axis, it is ensured that when a stress in a moment direction (torque direction), for example clockwise or counterclockwise, with the axis as a center is applied, no difference in torsional rigidity would be generated in any moment direction (in the direction of arrow H or J in FIG. 5).

In the related art in which a coil spring formed by spirally winding in one direction is applied, a difference in torsional rigidity would be generated depending on the moment direction (torque direction). As a result, in the case where a stress in the moment direction corresponding to a lower torsional rigidity is applied, the spring shows a greater deformation, which would be attended by a larger deformation of the outer tube.

As above-mentioned, the reinforcing spacer 52 being in a mesh form helps ensure that in whatever moment direction a stress may be applied on the outer tube 14 and the reinforcing spacer 52, the amount of deformation of the outer tube 14 is suppressed favorably. As a result, the outer tube 14 and the inner tube 12 can be advanced assuredly and smoothly into the lesion part in the lumen of the living body. In other words, the torsional rigidity is not varied depending on the direction of the moment force applied on the outer tube 14 and the reinforcing spacer 52, and a stable torsional rigidity can be obtained when a stress is applied in any of the clockwise direction (the direction of arrow H) and the counterclockwise direction (the direction of arrow J).

Furthermore, forming the reinforcing spacer 52 from an elastic resin material or the like helps ensure that when the inner tube 12 and the outer tube 14 are bent, the reinforcing spacer 52 is elastically deformed in the same manner as the tubes. Therefore, the reinforcing spacer 52 would not hamper movements of the inner tube 12 and the outer tube 14; naturally, this is favorable.

The detailed description above describes a stent delivery system disclosed by way of example. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system for indwelling a stent in a lumen of a living body, the stent delivery system comprising:
   an inner tube comprising a proximal tube and a distal tube, the distal tube being entirely distal to and spaced apart from the proximal tube by a space, the inner tube possessing an outer surface;
   a stent disposed on a distal-side outer surface of the inner tube and being compressed toward a center axis of the stent when inserted into a lumen of a living body, and restorable to a pre-compression expanded shape by being expanded outwardly when indwelled in the lumen of the living body;
   an outer tube containing the stent in an inner lumen of the outer tube and disposed outwardly of the inner tube so that an inner surface of the outer tube faces an outer surface of the inner tube, the outer tube being movable relative to the inner tube to release the stent to outside the outer tube by moving in a proximal direction relative to the inner tube;
   a reinforcing member movable in axial and radial directions relative to the outer tube and the inner tube, positioned between the outer tube and the inner tube entirely proximal to the stent, and the reinforcing member being a mesh-member having at least three through openings, the reinforcing member possessing an open distal end and an open proximal end, the open distal end and the open proximal end of the reinforcing member being free ends;
   a holding mechanism fixed to the outer surface of the inner tube so that the entire holding mechanism always moves together with the inner tube, the holding mechanism extending radially outwardly from the outer surface of the inner tube;
   a connecting member interconnecting the distal tube and the proximal tube, the connecting member extending within the space between the distal tube and the proximal tube in the axial direction;
   the entire reinforcing member being distal to the entire connecting member in the axial direction; and
   the entire reinforcing member being proximal to the entire holding mechanism in the axial direction.

2. The stent delivery system according to claim 1, wherein the reinforcing member is made from an elastic resin material, a metallic material or a mixed material comprised of both the elastic resin material and the metallic material.

3. The stent delivery system according to claim 1, wherein the reinforcing member is a hollow cylindrically shaped member possessing an inside diameter greater than an outside diameter of the inner tube.

4. The stent delivery system according to claim 1, wherein the reinforcing member is a hollow cylindrically shaped member possessing an outside diameter smaller than an inside diameter of the outer tube.

5. The stent delivery system according to claim 1, wherein the inner tube possesses a guide wire lumen extending between an open distal end and an open proximal end of the inner tube, the guide wire lumen being configured to receive a guide wire to guide movement of the stent delivery system, the open proximal end of the inner tube facing a guide wire leading-out opening in the outer tube through which the guide wire passes as the stent delivery system is being guided along the guide wire.

6. The stent delivery system according to claim 5, wherein the proximal-most end and the distal-most end of the reinforcing member are positioned distally of the guide wire leading-out opening.

7. The stent delivery system according to claim 1, wherein the inner surface of the outer tube is spaced from the outer surface of the inner tube so that a gap exists between the inner surface of the outer tube is spaced from the outer surface of the inner tube, the reinforcing member being positioned in the gap and possessing an outer surface spaced radially inward of the inner surface of the outer tube so that the reinforcing member is radially movable in the gap.

8. The stent delivery system according to claim 1, wherein the reinforcing member is movable relative to the inner tube and the outer tube before any movement of the outer tube relative to the inner tube.

9. The stent delivery system according to claim 1, wherein the reinforcing member possesses a distal-most end spaced apart from the proximal-most end of the holding mechanism so that a space exists between the distal-most end of the reinforcing member and the proximal-most end of the holding mechanism, and the reinforcing member is movable in an axial direction relative to the stent locking part to enter the space.

10. A stent delivery system for indwelling a stent in a lumen of a living body, the stent delivery system comprising:

an inner tube extending from a distal end to a proximal end in an axial direction;

an outer tube surrounding the inner tube so that a gap exists between an inner surface of the outer tube and an outer surface of the inner tube, the outer tube being movable relative to the inner tube in the axial direction;

a radially outwardly extending stent locking part fixed to the inner tube so that the stent locking part always moves together with the inner tube, the stent locking part being positioned between the distal end and the proximal end of the inner tube;

a radially inwardly compressed stent positioned in the gap between the inner surface of the outer tube and the outer surface of the inner tube so that the stent is covered by the outer tube, the stent being configured to expand outwardly in a radial direction upon the outer tube being moved proximally relative to the inner tube so that the stent is exposed, the stent possessing opposite distal and proximal ends both positioned distally of the stent locking part, the distal and proximal ends of the stent being free ends which are distal to the entirety of the stent locking part before the outer tube is moved proximally relative to the inner tube to expose the stent; and a reinforcing member positioned in the gap between the inner surface of the outer tube and the outer surface of the inner tube, the reinforcing member possessing proximal-most and distal-most open ends both positioned proximally of the entirety of the stent locking part, the stent locking part preventing the distal-most open end of the reinforcing member from moving distally to overlap with the stent locking part in the axial direction, the reinforcing member possessing a plurality of through holes and being configured to bend when the inner and outer tubes are bent, the entire reinforcing member being movable in the axial and radial directions relative to the stent locking part, the inner tube, and the outer tube before any relative movement between the outer tube and the inner tube.

* * * * *